United States Patent

Kurokawa

[11] Patent Number: 5,596,653
[45] Date of Patent: Jan. 21, 1997

[54] RADIATION THERAPY TREATMENT PLANNING SYSTEM

[75] Inventor: Masaaki Kurokawa, Amagasaki, Japan

[73] Assignee: Mitsubishi Denki Kabushiki Kaisha, Tokyo, Japan

[21] Appl. No.: 278,160

[22] Filed: Jul. 21, 1994

Related U.S. Application Data

[63] Continuation-in-part of Ser. No. 866,205, Apr. 9, 1992, abandoned.

[30] Foreign Application Priority Data

Apr. 9, 1991 [JP] Japan ................................. 3-103421

[51] Int. Cl.⁶ .............................. G06K 9/00; G06F 15/00
[52] U.S. Cl. ................. 382/128; 364/413.14; 364/413.26
[58] Field of Search .......................... 364/413.26, 413.14; 378/21, 4; 382/128

[56] References Cited

U.S. PATENT DOCUMENTS

| | | | |
|---|---|---|---|
| 3,987,281 | 10/1976 | Hodes | 364/413.26 |
| 4,455,609 | 6/1984 | Inamura et al. | 364/413.26 |
| 4,729,099 | 3/1988 | Iverson et al. | 364/413.26 |
| 5,027,818 | 7/1991 | Bova et al. | 364/413.14 |
| 5,291,404 | 3/1994 | Kurokawa | 364/413.26 |

OTHER PUBLICATIONS

"Computer Applications in Radiation Therapy Treatment Planning"; James A. Purdy; Radiation Medicine, vol. 1, No. 2, pp. 161–173, 1983.

Technical Paper of the 10th PC User Group Symposium, on Apr. 4, 1983, in Osaka Japan, pp. 1–13, "Computer Applications in Radiation Therapy Treatment Planning," James A. Purdy.

Primary Examiner—Leo Boudreau
Assistant Examiner—Matthew C. Bella
Attorney, Agent, or Firm—Rothwell, Figg, Ernst & Kurz

[57] ABSTRACT

A system for calculating the dose at a point of concern in a body has a data section for storing data concerning the irradiated radiation and a contribution distribution calculating section for calculating contribution factors. The contributing factors indicate the degree to which the respective neighboring points in the irradiated body contribute to the dose at the point of concern. The system also has a density distribution data section for storing data concerning the electron density at the respective neighboring points in the irradiated body which receives the therapy treatment and a region classification section for classifying the respective neighboring points in the typical models or the irradiated body. A dose calculating section calculates the dose at the point of concern on the basis of the contribution factors, the data in the density distribution data section, and the data in the region classification section.

24 Claims, 9 Drawing Sheets

RADIATION THERAPY TREATMENT PLANNING SYSTEM

This is a continuation-in-part of application Ser. No. 07/866,205, filed on Apr. 9, 1992, now abandoned.

BACKGROUND OF THE INVENTION

The present invention relates to a radiation therapy treatment planning system and method for planning radiation therapy treatment by calculating dose at the point of concern in a patient.

Figure 1:
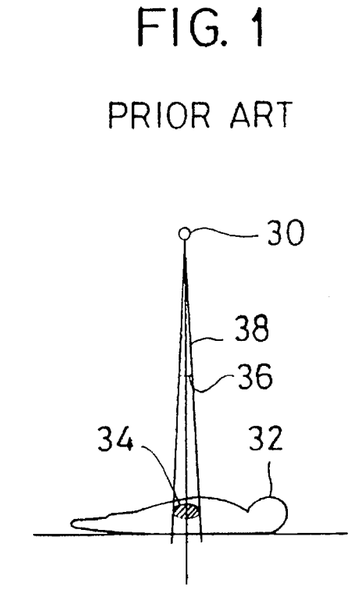
FIG. 1 is an explanatory diagram showing how the X-ray is irradiated onto a patient.

Radiation therapy is conducted in a manner shown in FIG. 1. As illustrated, X-ray 38 from a radiation source 30 is irradiated with an irradiation Field 36 onto a diseased part 34 of a patient 32. Before actually conducting X-ray irradiation, the dose which will be applied to the point of concern must be calculated. This calculation is however is not simple, because of Compton scattering.

Figure 2:
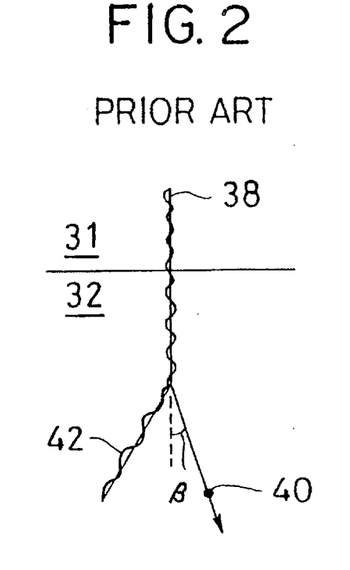
FIG. 2 is an explanatory diagram showing Compton scattering.

As shown in FIG. 2, X-ray 38 having entered from the air 31 into a patient 32 causes Compton scattering, by which X-ray 38 causes emission of electron 40, losing energy in the same amount given to the electron 40, and generating scattered X-ray 42 having a longer wavelength and proceeding in a different direction. The scattering angle $\beta$ is not greater than 90°. The dose is proportional to the number of ion pairs created by the passage of electrons through the region of concern.

Figure 3:
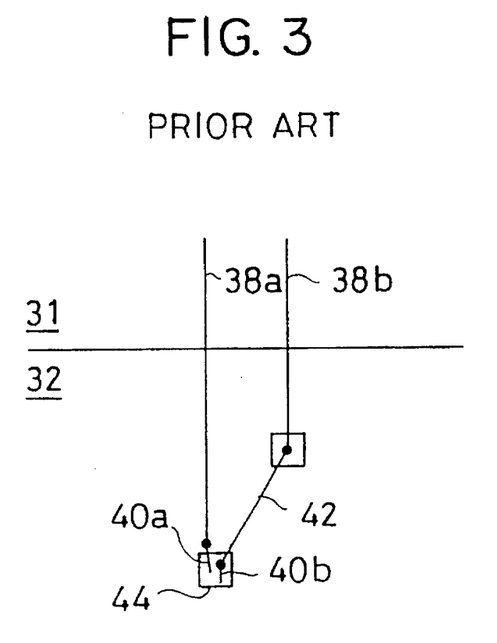
FIG. 3 is an explanatory diagram showing the classes of electrons reaching the point of concern.

For determining the dose in a region 44, shown in FIG. 3, various categories or classes, classified in accordance with the history from which the electrons have been generated, must be considered. The first class consists of the electron 40a due to the Compton scattering of incident X-ray 38a. The second class consists of the electron 40b due to Compton scattering off scattered X-ray 42 derived from incident X-ray 38b. The third class includes all other electrons, i.e., electrons, not illustrated, derived through more than two Compton scatterings.

Because the electrons are generated by Compton scatterings in the neighboring regions, consideration needs to be given to the contributions from respective neighboring points to the point off concern in determining the dose at the point of concern.

Conventional methods off calculating dose taking account of the contributions from the neighboring points includes the Monte Carlo method, the convolution method, the delta volume method, the equivalent tissue air ratio (ETAR) method, the power law method, the scatter air ratio (SAR) method, carlo tissue air ratio (RTAR) method. Some of these methods are summarized in James A. Purdy, Computer Applications in Radiation Therapy Treatment Planning, Radiation Medicine, Vol. 1, No. 2, pp. 161–173, 1983.

The Monte Carlo method or the like in which 3-dimensional calculation is conducted will produce accurate results, but takes too long a time for the calculation. In the ETAR method and the like in which the 2-dimensional calculation is conducted, the time required for the calculation is short, but the accuracy of calculation is relatively low, so that it sometimes is impossible to satisfy the accuracy requirement, such as the one prescribed by the recommendation by ICRU (International Commission on Radiation Units and Measurements) of restraining the error in the dose to be within ±5%.

SUMMARY OF THE INVENTION

An object of the invention is to provide a radiation therapy treatment planning system and method which can reduce the error in the dose calculation, and which can reduce the time required for the dose calculation.

A radiation therapy treatment planning system for calculating the dose at a point of concern irradiated with X-ray according to one aspect of the invention comprises a computer. The computer includes: an X-ray data section for storing X-ray data which concern the X-ray from the X-ray source and are obtained in advance by measurement; a contribution distribution calculating section for calculating, on the basis of the X-ray data stored in the X-ray data section, contribution factors indicating the degree to which the respective neighboring points in the body of the patient contribute to the dose at the point of concern; a density distribution data section for storing first electron density data at the respective neighboring points in the body of the patient on whom the radiation therapy treatment is planned, the first electron density data being obtained in advance by measurement; a region classification section for calculating, on the basis of second electron density data of a plurality of typical patient models in advance, classification data of respective neighboring points in each of the typical patient models depending on the class of the X-ray causing emission of electron beam which gives energy to the point of concern, for storing the classification data, and for selecting the classification data in connection with one of the typical patient models on the basis of the similarity with the first electron density data stored in the density distribution data section; and a dose calculating section for calculating the dose at the point of concern on the basis of the contribution factors calculated by the contribution distribution calculating section, the first electron density data stored in the density distribution data section, and the classification data of the typical patient model, selected in the region classification section.

A radiation therapy treatment planning system for calculating the dose at a point off concern irradiated with electron beam according to another aspect of the invention comprises a computer. The computer includes: an electron beam data section for storing electron beam data which concern the electron beam from the electron beam source and are obtained in advance by measurement; a contribution distribution calculating section for calculating, on the basis of the electron beam data in the electron beam data section, contribution factors indicating the degree to which the respective neighboring points in the irradiated body contribute to the dose at the point of concern; a density distribution data section for storing electron density data at the respective neighboring points in the body of the patient on whom the radiation therapy treatment is planned, the electron density data being calculated in advance by measurement; and a dose calculating section for calculating the dose at the point of concern on the basis of the contribution factors calculated by the contribution distribution calculating section, and the electron density data stored in the density distribution data section.

DETAILED DESCRIPTION OF THE PREFERRED EMBODIMENTS

Preferred embodiments or the invention will now be described.

First Embodiment

A first embodiment of a radiation therapy treatment planning system according to the invention will be described with reference to FIG. 4. The illustrated radiation therapy treatment planning system is for planning the X-ray radiation therapy treatment, and for this purpose it calculates, based on experimentally obtained data, the dose at the point of concern. In determining the dose at each point of concern, it takes account of the contributions due to Compton scattering at neighboring points.

The system comprises a computer 11 which includes a X-ray data section 1, a contribution distribution calculating section 2, a density distribution tiara section 3, a region classification section 4, and a dose calculating section 5.

The X-ray data section 1 stores field factors $F_A$ and tissue peak dose ratio (TPR) values having been obtained by measurements in advance.

The contribution distribution calculating section 2 is for calculating contribution factors indicative of the degree to which the respective neighboring points other than the point of concern contribute to the dose at the point of concern. The contribution factors as described herein are independent off the anatomic information. That is, the contribution factors are dependent on the geometric relationship between the point of concern and the neighboring point (whose contribution is considered) assuming that these points are in a homogeneous phantom, usually water.

The density distribution data section 3 stores density distribution data of the particular patient on whom the radiation therapy treatment is planned. The density distribution data include electron density data, and are obtained by measurement in advance.

The region classification section 4 is for classifying the region (namely, calculating classification data of respective neighboring points) in accordance with the category or class of the radiations contributing to the dose at the point off concern in each of a plurality of typical patient models, for storing the calculated classification data, and for selecting the classification data in connection with one of the typical patient models. Specifically, it provides the classification data indicating the class to which the each of the points belong, in each of the typical patient models that is selected. The selection is made in accordance with the, similarity to the electron density data in connection with the particular patient for which the radiation therapy treatment is planned.

The dose calculating section 5 receives the contribution factors from the contribution distribution calculating section 2, the electron density data from the density distribution data section 3 and the classification data from the region classification section 4, and calculates the dose at the point off concern.

Figure 5:
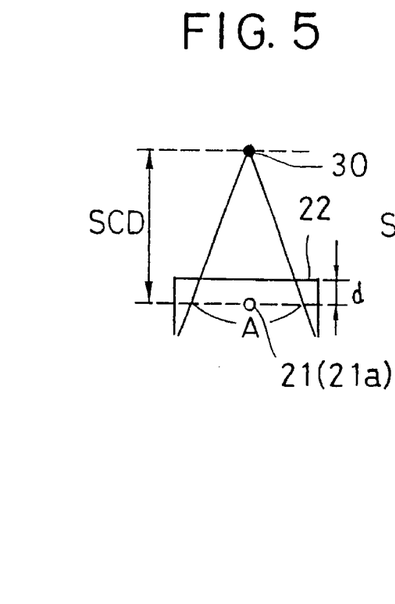
FIG. 5 is an explanatory diagram showing the method of measuring the tissue peak close ratio.

A method for measuring the field factors $F_A$ and TPR values stored in the X-ray data section 1 will first be described with reference to FIG. 5. A dose detector 21 is placed in water 22, used as a phantom, while an X-ray source 30 is positioned in air, directly over the detector 21 such that direct radiation from the X-ray source 30 to the detector 21 is normal to the surface of water 22. Through the following experiments, data which will be used to calculate the contribution of the respective neighboring points in water 22 to the point at which the detector 21 is positioned will be obtained. The point at which the detector 21 is positioned will therefore be referred to as the point of concern 21a.

The distance (sensor chamber distance) SCD between the detector 21 and a X-ray source 30 is maintained constant throughout a series of measurements.

The depth d of the detector 21 in water 22, and the equivalent irradiation field area A are varied in the manner described later, and the dose is measured or detected by the detector 21 for various values or depth d and equivalent field area A. The depth at which the dose is maximum is called a reference depth $d_r$, and this maximum dose is denoted by Dr(A). The field factor $F_A(A)$ is defined by the following equation (1).

$$F_A(A) = \frac{Dr(A)}{Dr(10 \times 10)} \quad (1)$$

In the above equation, Dr(10×10) is the dose at the reference depth $d_r$ when the field area A is 10 cm×10 cm.

The TPR value TPR(d, A) for the point of concern at a depth d with the equivalent field area A is defined by the following equation (2).

$$TPR(d, A) = \frac{D(d, A)}{Dr(A)} \quad (2)$$

From all the measured value of D(d, A) for various values of d and A, $d_r$ and Dr(A) are determined, and then the field factor $F_A(A)$ and TPR value are determined in accordance with the equations (1) and (2). These values are stored as measured data in the X-ray data section 1.

The contribution distribution calculating section 2 will next be described. From the equations (1) and (2), the following equation (3) holds.

$$\begin{aligned} D(d, A) &= Dr(A) \cdot TPR(d, A) \\ &= F_A(A) \cdot Dr(10 \times 10) \cdot TPR(d, A) \end{aligned} \quad (3)$$

If D(d, A) is set at i for simplifying the subsequent calculation, such setting is justified because it does not affect the essence of the process as what are obtained are relative contributions from the respective points, the equation (3) can be rewritten into the equation (4).

$$D(d, A) = F_A(A) \cdot TPR(d, A) \quad (4)$$

The calculation of the contribution factor η, which is conducted the contribution distribution calculating section 2 of the computer 11, will next be described with reference to FIG. 6. It will be observed that, because of the symmetry about the line connecting the X-ray source 30 and the point of concern 21a, i.e., radiation axis 29, contribution per unit volume from a given point, at a height difference d above the point of concern 21a and on the periphery of a circle having a radius r from the radiation axis 29, to the dose at the point of concern 21a can be obtained by determining the contribution from an annular part at a height difference d above the point of concern 21a, having a minute depth (height) $\Delta d$, having a radius r, and having a minute radial dimension $\Delta r$, and then dividing the contribution by the volume a $\Delta V$ of the annular part. Moreover, it is known that the contribution from an annular part at a height difference d above the point of concern 21a and having a radius r is equal to the contribution from the periphery (four sides) off a square part centered at the radiation axis, disposed at a height difference d above the point of concern 21a, having a side length $2r$, having a depth (height) $\Delta d$ and having a width (dimension perpendicular to the direction of each side and to the direction or the depth) $\Delta r$. The latter relationship is utilized when the field area is square, as is often the case.

In view of the equation (4), the dose D(d+$\Delta d$, A) at the point of concern 21a, when the depth of the point of concern 21a is d+$\Delta d$ and the field area at a height difference d above the point of concern 21a is A, is given by the following equation (5).

$$D(d+\Delta d, A) = F_A(A) \cdot TPR(d+\Delta d, A) \quad (5)$$

The dose D(d+$\Delta d$, A) is due to Compton scattering in the irradiated conical region having an equivalent field area A at a height of the point of concern 21a.

Of the dose D(d+$\Delta d$, A), the dose $D_{d,A}$ due to the region below the height d above the point of concern 21a is given by the following equation (6).

$$D_{d,A} = F_A(A) \cdot TPR(d, A) \cdot \exp(-\mu \Delta d) \quad (6)$$

In the above equation, $\mu$ denotes the X-ray absorption coefficient, and exp($-\mu \Delta d$) denote the effect of attenuation of the X-ray due to the passage of the X-ray through the disk of a thickness $\Delta d$.

Figure 6:
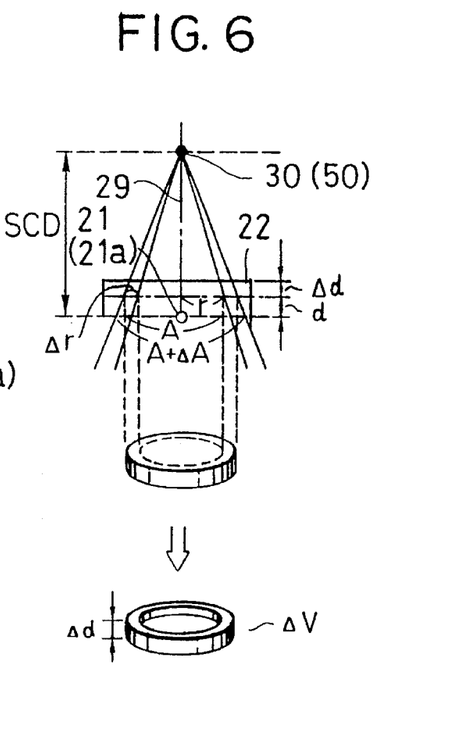
FIG. 6 is an explanatory diagrams showing the method of calculating the contribution factors.

The dose $D_{\Delta d, A}$ at the point of concern 21a due to Compton scattering in the disk-shaped region of a thickness $\Delta d$ as shown in FIG. 6 is given by the following equation (7).

$$\begin{aligned} D_{\Delta d, A} &= D(d + \Delta d, A) - D_{d, A} \quad (7) \\ &= F_A(A) \cdot TPR(d + \Delta d, A) - \\ & \quad F_A(A) \cdot TPR(d, A) \cdot \exp(-\mu \Delta d) \end{aligned}$$

The dose D(d+$\Delta d$, A+$\Delta A$) at the point of concern 21a at a depth d+$\Delta d$, when the equivalent field area of irradiation at a height of the point of concern 21a is A+$\Delta A$, is given by the following equation (8).

$$D(d+\Delta d, A+\Delta A) = F_A(A+\Delta A) \cdot TPR(d+\Delta d, A+\Delta A) \quad (8)$$

The dose D(d+$\Delta d$, A+$\Delta A$) is due to Compton scattering in the irradiated conical region having an equivalent field area off irradiation A+$\Delta A$ at a height of the point of concern 21a.

Of the dose D(d+$\Delta d$, A+$\Delta A$), the dose $D_{d, A+\Delta A}$ due to the region below the height d above the point of concern 21a is given by the following equation (9).

$$D_{d, A+\Delta A} = F_A(A+\Delta A) \cdot TPR(d, A+\Delta A) \cdot \exp(-\mu \Delta d) \quad (9)$$

The dose $D_{\Delta d, A+\Delta A}$ at the point of concern 21a due to Compton scattering in the disk-shaped region of a thickness $\Delta d$ shown in FIG. 6 is given by the following equation (10).

$$\begin{aligned} D_{\Delta d, A+\Delta A} &= D(d + \Delta d, A + \Delta A) - D_{d, A+\Delta A} \quad (10) \\ &= F_A(A + \Delta A) \cdot TPR(d + \Delta d, A + \Delta A) - \\ & \quad F_A(A + \Delta A) \cdot TPR(d, A + \Delta A) \cdot \exp(-\mu \Delta d) \end{aligned}$$

The dose $D_{\Delta d, \Delta A}$ due to Compton scattering in the annular part of a height $\Delta d$ and a volume $\Delta V$ as shown in the bottom of FIG. 6 is given by the following equation (11).

$$D_{\Delta d, \Delta A} = D_{\Delta d, A+\Delta A} - D_{\Delta d, A} \quad (11)$$

Dividing the dose $D_{\Delta d, \Delta A}$ by the volume of the annular part will give the dose from the annular part per unit volume. This value is defined as the contribution factor $\eta(d, A)$ which indicates the degree to which the point in the annular part at the outer periphery of a circular part having a radius r and displaced by a distance d toward the X-ray source 30 away from the point of concern 21a. That is, this value is defined by the following equation (12).

$$\begin{aligned} \eta(d, A) &= D_{\Delta d, \Delta A}/\Delta V \quad (12) \\ &= [F_A(A + \Delta A) \cdot \{TPR(d + \Delta d, A + \Delta A) - \\ & \quad TPR(d, A + \Delta A) \cdot \exp(-\mu \Delta d)\} - \\ & \quad F_A(A) \cdot \{TPR(d + \Delta d, A) - \\ & \quad TPR(d, A) \cdot \exp(-\mu \Delta d)\}]/\Delta V \end{aligned}$$

The above calculations of the equations (3) to (12) are performed in the contribution distribution calculating section 2 and the results of the calculations are stored in the contribution factor distribution calculating section 2.

Figure 7:
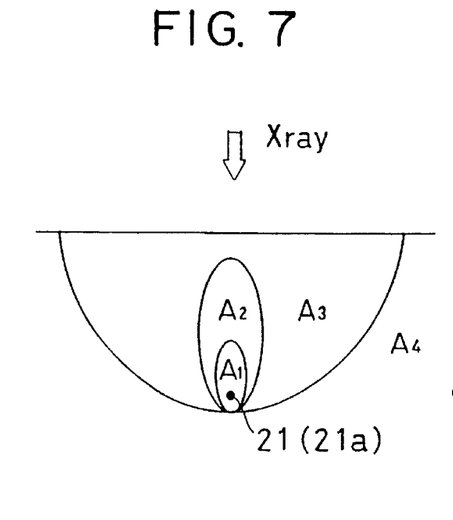
FIG. 7 and FIG. 8 are explanatory diagrams showing the classification of the contributing regions.

The region classification section 4 will next be described. An example of the regions divided by the region classification section 4 is shown in FIG. 7. The region classification section 4 classifies the contributing region which contributes to the dose at the point of concern 21a with respect to typical patient models. The classification is made in terms of the principal radiation which causes emission of electron beam giving energy to the point of concern 21a, that is whether such principal radiation is the direct radiation from the X-ray source, the first scattered ray due to the Compton scattering of the direct radiation, or the multiple scattered ray due to the Compton scattering of the first or subsequent scattered ray.

The classification of the contributing region may be made by the Monte Carlo method on typical patient models. In FIG. 7, the contribution region which the principal radiation is the direct radiation is indicated by reference $A_1$, the contribution region of which the principal radiation is the first scattered ray is denoted by reference $A_2$, the contribution region of which the principal radiation comprises both the first scattered ray and the multiple scattered ray is denoted by $A_3$, and the contribution region of which the principal radiation is the multiple scattered cay is denoted by $A_4$.

The density distribution data section 3 will next be described. The density distribution data section 3 stores the data, such as electron density data, calculated in advance based on the darkness of the CT (computed tomography) image of the particular patient on whom the radiation therapy treatment is planned.

The electron density $\rho_{ijk}$ at a point (i,j,k) is determined on the darkness of the CT image, i.e., the density of the tissue of the patient, for each of a plurality of points distributed throughout the region receiving the irradiation, and stored in the density distribution data section 3.

Figure 8:
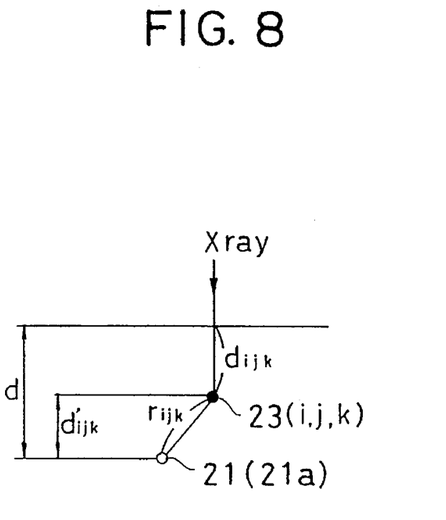

The density distribution data section 3 also stores the electron density correction coefficient H($r_{ijk}$) accounting for the absorption in the tissue of the X-ray directed to the point of concern 21a. Such absorption will next be explained with reference to FIG. 8. When the X-ray is incident on a contributing point 23 (with coordinate values (i,j,k)) at a depth $d_{ijk}$, and causes Compton scattering at the point 23, and the scattered X-ray is directed to the point off concern 21a. $r_{ijk}$ denotes the distance from the contributing point 23 to the point of concern 21a, and the electron density corrected length is $r_{1ijk}$. The depth of the contributing point 23 is $d_{ijk}$, and the electron density corrected length is $d_{1ijk}$. Where the radiation which causes emission of electrons giving energy to the point of concern 21a is the direct radiation, $r_{ijk}$ is 0, so that $H(r_{ijk})=1$. Where the radiation causing emission of electrons giving energy to the point of concern 21a is the first scattered ray as shown in FIG. 8, the density correction coefficient $H(r_{ijk})$ is given by the following equation (13).

$$H(r_{ijk}) = \exp\{-\mu(r_{ijk} - r_{1ijk})\} \quad (13)$$

The dose calculating section 5 calculates the dose D(d, A) at the point of concern 21a at a depth d with the equivalent field area being A, in accordance with the following equation (14), based on the contribution factor $\eta(d_{ijk}, A_{ijk})$ from the contribution distribution calculating section 2, data $\rho_{ijk}$ and $H(r_{ijk})$ on the electron density from the density distribution data section 3, and the classification data from the region classification section 4. The region classification section 4 selects the classification data in connection with one of the typical patient models on the basis of the similarity with the data of the particular patient on whom the radiation therapy treatment is planned.

$$D(d, A) = C \cdot \sum_{ijk} \{\rho_{ijk} \cdot \eta(d'_{ijk}, A_{ijk}) \cdot \exp(-\mu\, d_{1ijk}) \cdot \Delta v \cdot H(r_{ijk})\} \quad (14)$$

In the equation (14), $\exp(-\mu d_{1ijk})$ denotes the effect of attenuation of the X-ray through the depth $d_{ijk}$ shown in FIG. 8, $\Delta v$ denotes the volume of the pixel at a point (i,j,k), $C=Dr(10\times10)$, and $d'_{ijk}=d-d_{ijk}$.

Figure 9:
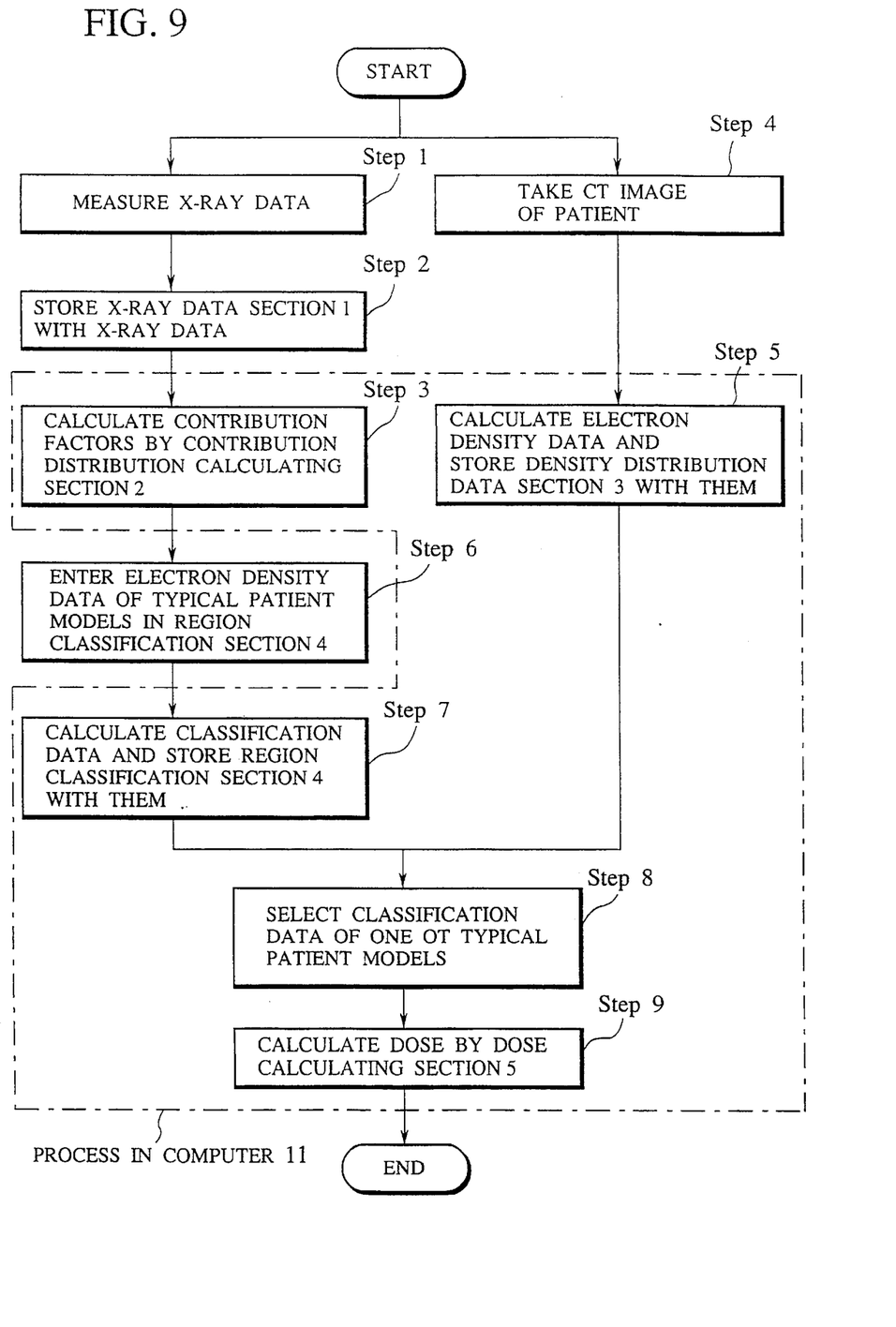
FIG. 9 is a flowchart showing a radiation therapy treatment method using the system of FIG. 4.

A radiation therapy treatment planning method using the system or FIG. 4 will be described with reference to FIG. 9.

In this method, firstly, the X-ray data concerning the X-ray from the X-ray source is measured in advance by a detector 21 (Step 1), and the X-ray data are stored in the X-ray data section 1 of the computer 11 (Step 2). Next, contribution factors are calculated, on the basis of the X-ray data in the X-ray data section 1 by a contribution distribution calculating section 2 of the computer 11 (Step 3).

On the other hand a CT image off the body of the patient on whom the radiation therapy treatment is planned is taken (Step 4), and the electron density data at the respective neighboring points in the body of the patient are calculated in advance on the basis of the darkness in the CT image of the body of the patient (Step 5) and stored in the density distribution data section 3 of the computer 11 (Step 5).

The electron density data of a plurality of typical patient models is entered in the region classification section 4 of the computer 11 (Step 6), the classification data are calculated, on the basis of the electron density data of a plurality of typical patient models in advance by the region classification section 4 and stored in the region classification section 4 (Step 7).

Next, the classification data in connection with one of the typical patient models is selected on the basis of the similarity with the first electron density stored in the density distribution data section 3 by the region classification section 4 (Step 8) and the dose at the point of concern is calculated on the basis off the contribution factors calculated by the contribution distribution calculating section 2, the first electron density data stored in the density distribution data section 3, and the classification data of the typical patient model selected in the region classification section 4 by a dose calculating section 5 off the computer 11 (Step 9).

As has been described, in this embodiment, the TPR values and the field factors which are dependent on the energy and the field area of the X-ray are obtained by measurement in advance, and contribution factors are calculated on the basis of these TPR values and the field factors, and the dose is calculated using the contribution factors. As a result, the time required or calculation is short. Moreover, since the dose calculation using the contribution factors is a three-dimensional calculation, the error in the dose calculation is smaller than if the conventional two-dimensional calculation is employed.

In the above embodiment, the region is divided for a plurality of typical patient models, and one of the models which is most similar is selected, and the data of the selected model are used for the calculation, the time required for the calculation is further reduced.

In the above embodiment, TPR values are used for the calculation of the contribution factors $\eta$, but tissue-air ratio (TAR) or percentage depth dose (PDD) data may be used in place of the TPR values.

When TAR values are used, the contribution factors used in the equation (14) are given by the following equation (15).

$$\eta(d, A) = \left[\frac{F_A(A + \Delta A)}{F_S(A + \Delta A)} \cdot \{TAR(d + \Delta d, A + \Delta A) - \right.$$

$$TAR(d, A + \Delta A) \cdot \exp(-\mu\, \Delta\, d)\} -$$

$$\frac{F_A(A)}{F_S(A)} \cdot \{TAR(d + \Delta d, A) -$$

$$\left. TAR(d, A) \cdot \exp(-\mu\, \Delta\, d)\}\right]/\Delta V \quad (15)$$

In the above equation, $F_S(A)$ denotes a scatter factor for the equivalent field area A, and $F_S(A+\Delta A)$ denotes a scatter factor for the equivalent field area $A+\Delta A$.

$$\eta(d, A) = [F_A(A + \Delta A) \cdot \{PDD(d + \Delta d, A_0 + \Delta A_0) - \quad (16)$$

$$PDD(d, A_0 + \Delta A_0) \cdot \exp(-\mu'\, \Delta d)\}/100 -$$

$$F_A(A) \cdot \{PDD(d + \Delta d, A_0) -$$

$$PDD(d, A_0) \cdot \exp(-\mu'\, \Delta d)\}/100] \cdot$$

$$\{(f + d)/(f + d_r)\}^2/\Delta V$$

In the above equation, f denotes a sensor surface distance (SSD) between the X-ray source and the surface of water.

Second Embodiment

Figure 10:
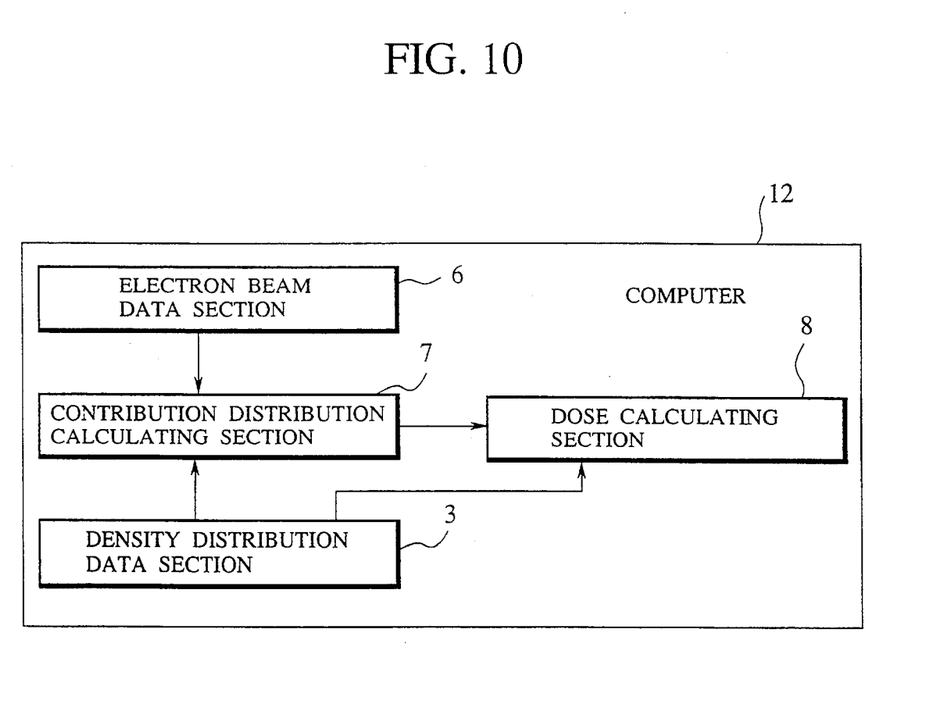
FIG. 10 is a block diagram showing a radiation therapy treatment planning system of a second embodiment of the invention.

A second embodiment of the invention will now be described with reference to FIG. 10. The radiation therapy treatment planning system of this embodiment is for use in connection with electron beam therapy treatment. It comprises a computer 12 which includes an electron beam data section 6, a contribution distribution calculating section 7, a density distribution data section 3, and a dose calculating section 8.

The electron beam data section 6 stores data such as field factors $F_A$ and percentage depth doses (PDD) measured in advance. The contribution distribution calculating section 7 calculates the contribution factors indicating the degree to which the respective neighboring points contribute to the dose at the point of concern.

The density distribution data section 3 stores data concerning the electron density calculated on the basis of the density of the tissue off the patient on whom the radiation therapy is planned.

The dose calculating section 8 calculates the dose at the point of concern on the basis of the contribution factors from the contribution distribution calculating section 7, and the data concerning the electron density from the density distribution data section 3.

Figure 11:
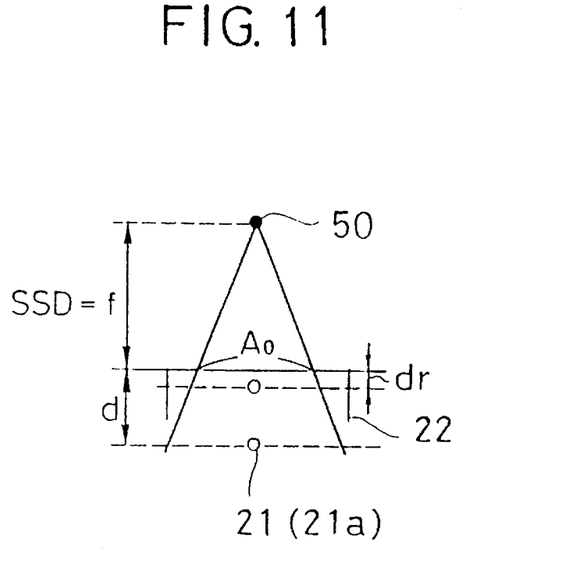
FIG. 11 and FIG. 12 are explanatory diagrams showing the method of measuring the percentage depth doses.

The PDD values are measured in the following manner. As illustrated in FIG. 11, a detector 21 is placed in water 22, and an electron beam source 50 is positioned directly over the detector 21 such that the electron beam which directly irradiates the detector 21 is normal to the surface of water 22. The electron beam source 50 is positioned at a distance (height difference) SSD from the surface of water 22. The dose is detected by the detector 21 as electron beam is irradiated toward the detector 21. The distance SSD is kept constant, while the depth d of the detector 21 in water is varied, and the measurements are made for a plurality off detector positions.

Assume that the dose at the detector 21 with the equivalent Field area at the surface of water being $A_0$ and the depth of the detector 21 being d is denoted by $D(d, A_0)$.

If the dose at the reference depth $d_r$ is denoted by $D_r(A)$, the percentage depth dose $PDD(d, A_0)$ is defined by the following equation (17).

$$PDD(d, A_0) = \frac{D(d, A_0)}{Dr(A_0)} \quad (17)$$

From all measured value of $D(d, A_0)$ for various values of d, $d_r$ and $D_r(A_0)$ are determined, anti then the field factor and PDD value are determined. These values are stored as measured data in the electron beam data section 6.

The contribution distribution calculating section 7 will next be described with reference to FIGS. 6, 10 and 11. As shown in the bottom of FIG. 6, the volume of the annular part of water is denoted by $\Delta V$ and the thickness (height) is denoted by $\Delta d$, then the contribution factor $\eta(d, A)$ which is the degree of contribution per unit volume of the annular part at a distance d from the detector 21 toward the sourc 50 contributes, to the dose at the point of concern 21a is given by the following equation (18).

$$\eta(d, A) = [F_A(A + \Delta A) \cdot \{PDD(d + \Delta d, A_0 + \Delta A_0) - \quad (18)$$
$$PDD(d, A_0 + \Delta A_0) \cdot \exp(-\mu' \Delta d)\}/100 -$$
$$F_A(A) \cdot \{PDD(d + \Delta d, A_0) -$$
$$PDD(d, A_0) \cdot \exp(-\mu' \Delta d)\}/100] \cdot$$
$$\{(f + d)/(f + d_r)\}^2/\Delta V$$

In the above equation, $\mu'$ represents electron beam absorption coefficient, $\exp(-\mu' \Delta d)$ represents the effect of attenuation of the electron beam through water of a thickness off $\Delta d$, f=SSD, and A denotes the equivalent field area at the height of the point off concern 21a. By substituting the following equations (19) and (20) into the equation (12) and replacing $\{(f+d+\Delta d)/(f+d_r)\}^2$ with $\{(f+d)/(f+d_r)\}^2$ for simplifying the equation, the above equation (18) can be derived.

$$TPR(d, A)=PDD(d, A_0)\cdot\{(f+d)/(f+d_r)\}^2/100 \quad (19)$$

$$TPR(d, A+\Delta A)=PPD(d, A_0+\Delta A_0)\cdot\{(f+d+\Delta d)/(f+d_r)\}^2/100 \quad (20)$$

Figure 4:
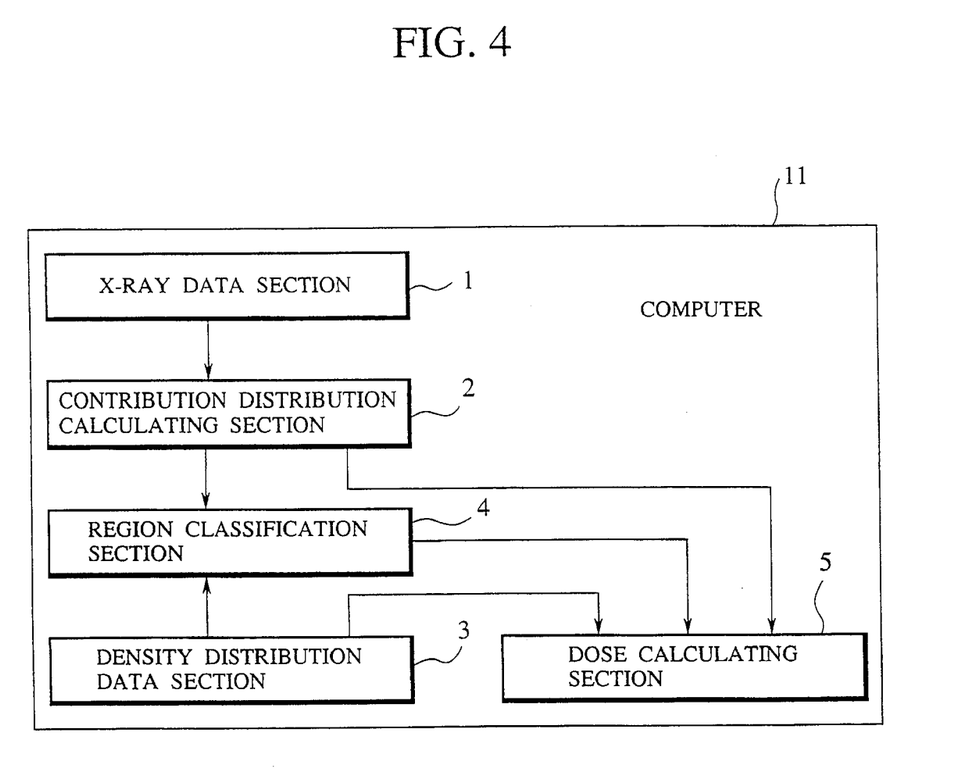
FIG. 4 is a block diagram showing a radiation therapy treatment planning system of a first embodiment of the invention.

Like the density distribution data section 3 in the embodiment of FIG. 4, the density distribution data section 3 of this embodiment stores electron density $\rho_{ijk}$ calculated in advance on the basis of the darkness of the CT image of the patient on whom the radiation therapy is planned.

The dose calculation section 8 calculates the dose D(d, A) at the point of concern at a depth d, with the equivalent field area A, on the basis of the contribution factors $\eta(d'_{ijk}, A_{ijk})$ from the contribution distribution calculating section 7, and the electron density $\rho_{ijk}$ from the density distribution data section 3 in accordance with the following equation (21).

$$D(d, A)=\Sigma_{ijk}\{\rho_{ijk}\cdot\eta(d'_{ijk}, A_{ijk})\cdot\Delta v\cdot\exp(-\mu'd_{1ijk})\} \quad (21)$$

In the above equation, $\Delta v$ represents the volume of the pixel at a point (i,j,k), and $d_{1ijk}$ represents the electron density corrected length. Since the electrons reach the point concern 21a after having experienced one or more scattering, the electron density in the vicinity of the line connecting the point (i,j,k) to the point of concern 21a contributes to the increase in the dose at the point of concern. This is because the electron beam causes emission of electrons in the irradiated body (patient) by scattering, and the emitted electrons also contributes to the dose at the point of concern. The region from which electron beam contributing the dose at the point of concern is emitted is called a sensitivity region, and extends, for example, as indicated by $A_e$ in FIG. 12. The maximum sensitive distance Rmax of the sensitivity region $A_e$ is dependent on the energy of the electron beam, and is given by the following equation (22).

$$Rmax \text{ [cm]}=0.542 \text{ [cm/MeV]}\times E \text{ [MeV]}-0.133 \text{ [cm]} \quad (22)$$

Figure 12:
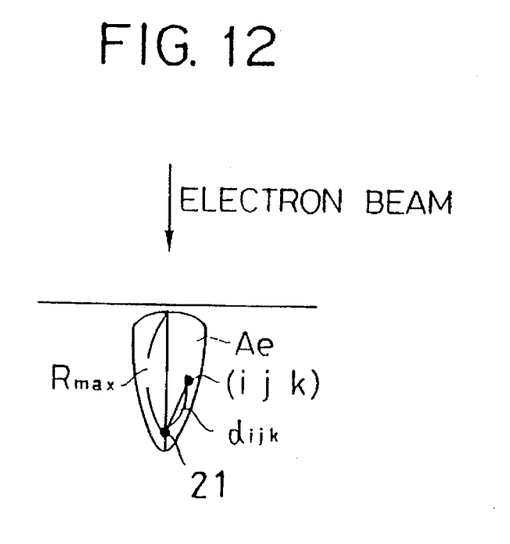

For an electron beam of 10 MeV, Rmax is about 5.3 cm.

When electron beam enters the irradiated body, X-ray due to bremsstrahung of the electron beam may cause Compton scattering, and thereby emitting electrons and contributing to the dose at the point of concern 21a. Such phenomenon may occur outside the sensitivity region $A_e$. However, if the energy of the electron beam is less than 10 MeV, such effects is negligible.

Figure 13:
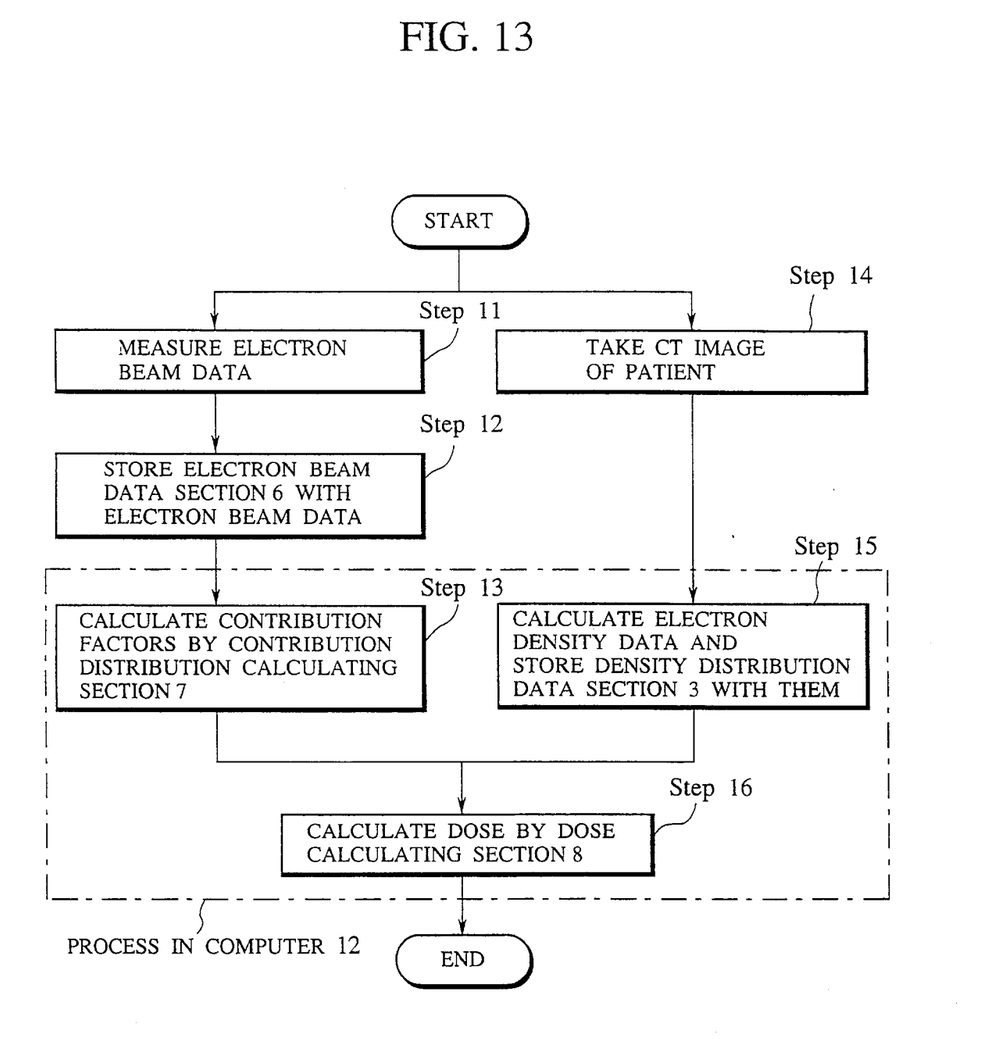
FIG. 13 is a flowchart showing a radiation therapy treatment method using the system of FIG. 10.

A radiation therapy treatment planning method using the system of FIG. 10 will be described with reference to FIG. 13.

In this method, firstly, electron beam data concerning the electron beam from the electron beam source is measured in advance by a detector 21 (Step 11), and the electron beam data data are stored in the electron beam data section 6 of a computer 12 (Step 12). Next, contribution factors are calculated, on the basis of the electron beam data in the electron beam data section 6 by a contribution distribution calculating section 7 of the computer 12 (Step 13).

On the other hand, a CT image off the body of the patient on whom the radiation therapy treatment is planned is taken (Step 14), and the electron density data at the respective neighboring points in the body of the patient are calculated in advance on the basis of the darkness in the CT image of the body of the patient (Step 15) and stored in the density distribution data section 3 of the computer 12 (Step 15).

The dose at the point of concern is calculated on the basis of the contribution factors calculated by the contribution distribution calculating section 8, the first electron density data stored in the density distribution data section 3, and the classification data of the typical patient model selected in the region classification section 4 by a dose calculating section 8 of the computer 12 (Step 16).

As has been described, in the above embodiment, the PDD values and the field factors dependent on the energy of the electron beam source 50 and the irradiation field are obtained in advance by measurement, and contribution factors are calculated from the PDD values and the field factors, and the dose is calculated on the basis of the PDD values and the field factors. The close calculation on the basis of the contribution factor is a three-dimensional calculation, so the error is smaller than in the conventional two-dimensional calculation.

Third Embodiment

Figure 14:
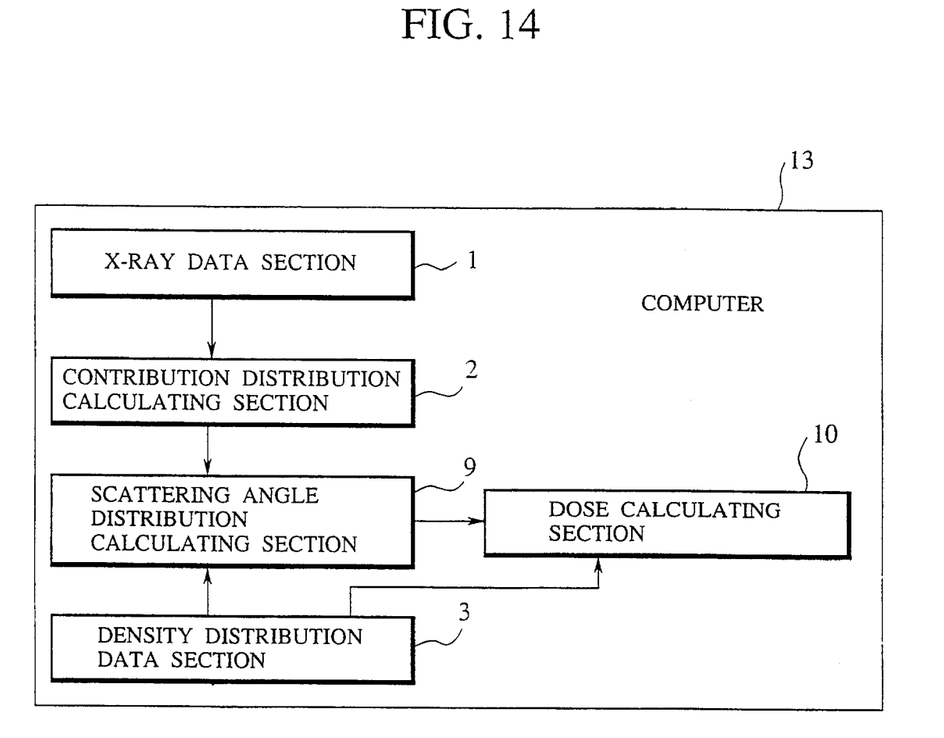
FIG. 14 is a block diagram showing a radiation therapy treatment planning system of a third embodiment of the invention.

A third embodiment of the invention will now be described with reference to FIG. 14. The radiation therapy treatment planning system is for use in connection with X-ray radiation therapy. It comprises a computer 13 which includes an X-ray data section 1, a contribution distribution calculating section 2, a density distribution data section 3, a scattering angle distribution calculating section 9, and a dose calculating section 10.

The X-ray data section 1 stores data such as field factors and TPR values which are obtained by measurement in advance. The contribution distribution calculating section 2 calculates contribution factors. The density distribution data section 3 stores data concerning the electron density calculated on the basis of the density off the tissue of the patient on whom the radiation therapy is planned. The X-ray data section 1, the contribution distribution calculating section 2, and the density distribution data section 3 may be the same as those shown in FIG. 4.

The scattering angle distribution calculating section 9 calculates the scattering angle distribution f(θ) on the basis of the contribution factor calculated in the contribution factor calculating section 2.

The dose calculating section 10 calculates the dose at the point off concern on the basis of the scattering angle distribution f(θ) and the data concerning the electron density from the density distribution data section 3.

Figure 15:
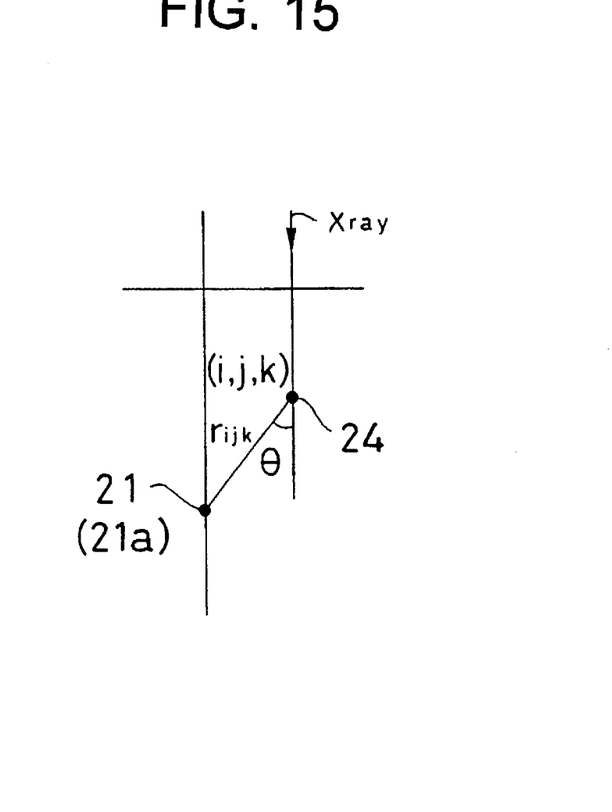
FIG. 15 is an explanatory diagram showing the scattering angle.
Figure 16:
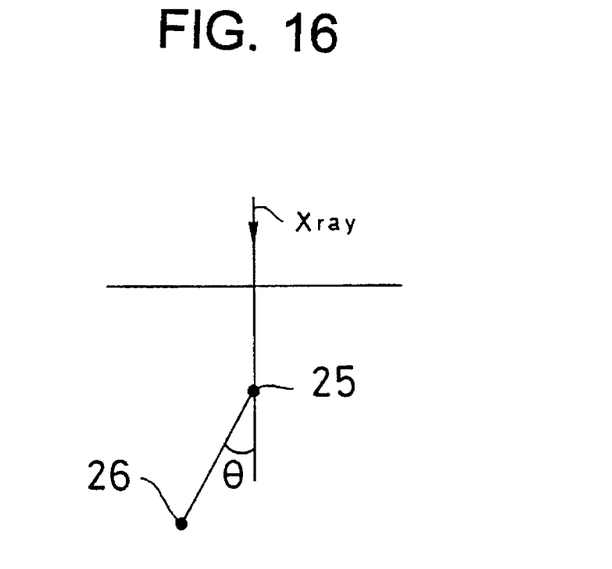
FIG. 16 is an explanatory diagram showing the relationship between the operating point and other point.

The contribution to the point of concern 21a in the region $A_2$ shown in FIG. 7 was mainly that of the first scattered ray. If the scattering angle distribution f(θ) is set as:

$$f(\theta) = \eta(d_{ijk}, A_{ijk}) \cdot r_{ijk}^2 \quad (23)$$

then using the contribution factor η of scattering point 24 in the region $A_2$ shown in FIG. 15 (the point from which the scattered ray reaches the point off concern at an incident angle θ), f(θ) can be determined. With regard to the multiple scattered ray, the contribution factors η for the region $A_4$ can be used. By using the scattering angle distribution f(θ) thus obtained, the dose can be determined by the ETAR method or the like.

Where the convolution method is used for the homogenous correction of the direct beam, the distribution in the region $A_1$ may be used, and the effects from the operating point 25 to other point 26 can be utilized. The operating means the point at which the direct beam act with each other or the scattering point.

In the prior art, f(θ) was obtained using the Klein-Nishina equation for Compton scattering, or the like, When this equation is used, it is necessary to account for the effects of the multiple scattering. It is therefore difficult to accurately express f(θ). Where the linac is used, the X-ray has a spectrum, so that the difficulty is added. When the convolution method is used to accurately calculate f(θ), the Monte Carlo method must be used, so that the process of calculation is complicated, and the time taken for achieving the required accuracy is long.

In the present embodiment, the contribution distribution data section 2 uses the data in the X-ray data section 1, to obtain the contribution factor η, in the same way as the First Embodiment. The scattering angle distribution calculating section 9 calculates the scattering angle f(θ) in accordance with the equation (23) by referring to the data in the density distribution section 3. The dose calculating section 10 calculates the dose by the ETAR method or the like using the scattering angle distribution f(θ) that has been calculated.

The scattering angle distribution f(θ) calculated in the manner described above may also be used in delta volume method.

According the third embodiment, the scattering angle distribution is calculated using the contribution factor distribution, so the close calculation using ETAR method or the like can be made accurately, in a short time.

What is claimed is:

1. A radiation therapy treatment planning system for calculating dose at a point of concern in a body of a patient irradiated with X-ray from an X-ray source, in a radiation therapy treatment, comprising a computer;

the computer including:
an X-ray data section for storing X-ray data, including tissue peak dose ratios and field factors, which concern said X-ray from said X-ray source and are obtained in advance by measurement;
a contribution distribution calculating section for calculating, on the basis of said X-ray data stored in said X-ray data section, contribution factors indicating a degree to which respective neighboring points in the body of the patient contribute to the dose at point of concern;
a density distribution data section for storing first electron density data at the respective neighboring points in the body of the patient on whom the radiation therapy treatment is planned, said first electron density data being obtained in advance by measurement;
a region classification section for calculating, on the basis of second electron density data of a plurality of typical patient models in advance, classification data of respective neighboring points in each of the typical patient models depending on the class of the X-ray causing emission of electron beam which gives energy to the point of concern, for storing said classification data, and for selecting said classification data in connection with one of the typical patient models on the basis of the similarity with said first electron density data stored in said density distribution data section; and
a dose calculating section for calculating the dose at the point of concern on the basis of said contribution factors calculated by said contribution distribution calculating section, said first electron density data stored in said density distribution data section, and said classification data of the typical patient model selected in said region classification section.

2. The system of claim 1, wherein said first electron density data stored in said density distribution data section is obtained on the basis of a darkness in a computed tomography image of the body of the patient on whom the radiation therapy treatment is planned.

3. The system of claim 1, wherein said region classification section classifies the region in accordance with whether the principal X-ray causing emission of electron beam giving energy to the point of concern is the irradiated X-ray from said X-ray source, the first scattered X-ray due to Compton scattering caused by the irradiated X-ray from said X-ray source, or the multiple scattered X-ray having experienced more than one Compton scattering caused by the irradiated X-ray from said X-ray source.

4. The system of claim 1, wherein said region classification section selects one of the typical patient models which is most similar to the body of the patient on whom the radiation therapy treatment is planned, and outputs said classification data of the selected patient model to said dose calculation section.

5. A radiation therapy treatment planning method for calculating dose at a point of concern in a body of a patient irradiated with X-ray from an X-ray source, in a radiation therapy treatment, comprising the steps of:

measuring X-ray data, including tissue peak dose ratios and field factors, concerning said X-ray from said X-ray source in advance by a detector;

storing said X-ray data in an X-ray data section of a computer;

calculating, on the basis of said X-ray data stored in said X-ray data section by a contribution distribution calculating section of said computer, contribution factors indicating a degree to which respective neighboring points in the body of the patient contribute to the dose at the point of concern;

taking a computed tomography image of the body of the patient on whom the radiation therapy treatment is planned;

calculating first electron density data at the respective neighboring points in the body of the patient in advance on the basis of a darkness in the computed tomography image of the body of the patient;

storing a density distribution data section of said computer with said first electron density data;

entering second electron density data of a plurality of typical patient models in a region classification section of said computer;

calculating, on the basis of said second electron density data of a plurality of typical patient models in advance by said region classification section, classification data of respective neighboring points in each of the typical patient models depending on the class of the X-ray causing emission of electron beam which gives energy to the point of concern, and storing said region classification section with said classification data;

selecting said classification data in connection with one of the typical patient models on the basis of the similarity with said first electron density stored in said density distribution data section by said region classification section; and calculating the dose at the point of concern on the basis of said contribution factors calculated by said contribution distribution calculating section, said first electron density data stored in said density distribution data section, and said classification data of the typical patient model selected in said region classification section by a dose calculating section of said computer.

6. The method of claim 5, wherein the region classification section classifies the region in accordance with whether the principal X-ray causing emission of electron beam giving energy to the point of concern is the irradiated X-ray from said X-ray source, the first scattered X-ray due to Compton scattering caused by the irradiated X-ray from said X-ray source, or the multiple scattered X-ray having experienced more than one Compton scattering caused by the irradiated X-ray from said X-ray source.

7. The method of claim 5, wherein said region classification section selects one of the typical patient models which is most similar to the body of the patient on whom the radiation therapy treatment is planned, and outputs said classification data of the selected patient model to said dose calculation section.

8. A radiation therapy treatment planning system for calculating dose at a point of concern in a body of a patient irradiated with electron beam from an electron beam source, in a radiation therapy treatment, comprising a computer: the computer including:

an electron beam data section for storing electron beam data, including percentage depth doses and field factors, which concern said electron beam from said electron beam source and are obtained in advance by measurement;

a contribution distribution calculating section for calculating, on the basis of said electron beam data stored in said electron beam data section, contribution factors indicating a degree to which respective neighboring points in the body of the patient contribute to the dose at point of concern;

a density distribution data section for storing electron density data at the respective neighboring points in the body of the patient on whom the radiation therapy treatment is planned, said electron density data being calculated in advance by measurement; and a dose calculating section for calculating respective components of the dose to which the respective neighboring points within a sensitivity region, from which electrons contributing the dose at the point of concern are emitted due to the irradiated electron beam, contribute on the basis of said contribution factors at the respective neighboring points calculated by said contribution distribution calculating section, said electron density data at the respective neighboring points stored in said density distribution data section, and summing said components of the dose to obtain the dose at the point of concern.

9. The system of claim 8, wherein said electron density data of the patient stored in said density distribution data section is obtained on the basis of a darkness in a computed tomography image of the body of the patient on whom the radiation therapy treatment is planned.

10. A radiation therapy treatment planning method for calculating dose at a point of concern in a body of a patient irradiated with electron beam from an electron beam source, in a radiation therapy treatment, comprising steps of:

measuring electron beam data, including percentage depth doses and field factors, concerning said electron beam from said electron beam source in advance by a detector;

storing said electron beam data in an electron beam data section of a computer;

calculating, on the basis of said electron beam data stored in said electron beam data section by a contribution distribution calculating section of said computer, contribution factors indicating a degree to which respective neighboring points in the irradiated body contribute to the dose at the point of concern;

taking a computed tomography image of the body of the patient on whom the radiation therapy treatment is planned;

calculating electron density data at the respective neighboring points in the body of the patient in advance on the basis of a darkness in the computed tomography image of the body of the patient;

storing a density distribution data section of said computer with said electron density distribution data;

calculating, by a dose calculating section of said computer, respective components of the dose to which the respective neighboring points within a sensitivity region, from which electrons contributing the dose at the point of concern are emitted due to the irradiated electron beam, contribute on the basis of said contribution factors at the respective neighboring points calculated by said contribution distribution calculating section, and said electron density data at the respective neighboring points stored in said density distribution data section; and summing said components of the dose to obtain the dose at the point of concern by said dose calculating section.

11. A radiation therapy treatment planning system for calculating dose at a point of concern in a body of a patient irradiated with X-ray from an X-ray source, in a radiation therapy treatment, comprising a computer;

the computer including:

an X-ray data section for storing X-ray data, including tissue peak dose ratios, scatter factors and tissue air dose ratios, which concern said X-ray from said X-ray source and are obtained in advance by measurement;

a contribution distribution calculating section for calculating, on the basis of said X-ray data stored in said X-ray data section, contribution factors indicating a degree to which respective neighboring points in the body of the patient contribute to the dose at point of concern;

a density distribution data section for storing first electron density data at the respective neighboring points in the body of the patient on whom the radiation therapy treatment is planned, said first electron density data being obtained in advance by measurement;

a region classification section for calculating, on the basis of second electron density data of a plurality of typical patient models in advance, classification data of respective neighboring points in each of the typical patient models depending on the class of the X-ray causing emission of electron beam which gives energy to the point of concern, for storing said classification data, and for selecting said classification data in connection with one of the typical patient models on the basis of the similarity with said first electron density data stored in said density distribution data section; and a dose calculating section for calculating the dose at the point of concern on the basis of said contribution factors calculated by said contribution distribution calculating section, said first electron density data stored in said density distribution data section, and said classification data of the typical patient model selected in said region classification section.

12. A radiation therapy treatment planning system for calculating dose at a point of concern in a body of a patient irradiated with X-ray from an X-ray source, in a radiation therapy treatment, comprising a computer;

the computer including:

an X-ray data section for storing X-ray data, including tissue peak dose ratios and percentage depth doses, which concern said X-ray from said X-ray source and are obtained in advance by measurement;

a contribution distribution calculating section for calculating, on the basis of said X-ray data stored in said X-ray data section, contribution factors indicating a degree to which respective neighboring points in the body of the patient contribute to the dose at point of concern;

a density distribution data section for storing first electron density data at the respective neighboring points in the body of the patient on whom the radiation therapy treatment is planned, said first electron density data being obtained in advance by measurement;

a region classification section for calculating, on the basis of second electron density data of a plurality of typical patient models in advance, classification data of respective neighboring points in each of the typical patient models depending on the class of the X-ray causing emission of electron beam which gives energy to the point of concern, for storing said classification data, and for selecting said classification data in connection with one of the typical patient models on the basis of the similarity with said first electron density data stored in said density distribution data section; and a dose calculating section for calculating the dose at the point of concern on the basis of said contribution factors calculated by said contribution distribution calculating section, said first electron density data stored in said density distribution data section, and said classification data of the typical patient model selected in said region classification section.

13. The system of claim 11, wherein said first electron density data stored in said density distribution data section is obtained on the basis of a darkness in a computed tomography image of the body of the patient on whom the radiation therapy treatment is planned.

14. The system of claim 11, wherein said region classification section classifies the region in accordance with whether a principal X-ray causing emission of electron beam giving energy to the point of concern is the irradiated X-ray from said X-ray source, the first scattered X-ray due to Compton scattering caused by the irradiated X-ray from said X-ray source, or the multiple scattered X-ray having experienced more than one Compton scattering caused by the irradiated X-ray from said X-ray source.

15. The system of claim 11, wherein said region classification section selects one of the typical patient models which is most similar to the body of the patient on whom the radiation therapy treatment is planned, and outputs said classification data of the selected patient model to said dose calculation section.

16. The system of claim 12, wherein said first electron density data stored in said density distribution data section is obtained on the basis of a darkness in a computed tomography image of the body of the patient on whom the radiation therapy treatment is planned.

17. The system of claim 12, wherein said region classification section classifies the region in accordance with whether the principal X-ray causing emission of electron beam giving energy to the point of concern is the irradiated X-ray from said X-ray source, the first scattered X-ray due to Compton scattering caused by the irradiated X-ray from said X-ray source, or the multiple scattered X-ray having experienced more than one Compton scattering caused by the irradiated X-ray from said X-ray source.

18. The system of claim 12, wherein said region classification section selects one of the typical patient models which is most similar to the body of the patient on whom the radiation therapy treatment is planned, and outputs said classification data of the selected patient model to said dose calculation section.

19. A radiation therapy treatment planning method for calculating dose at a point of concern in a body of a patient irradiated with X-ray from an X-ray source, in a radiation therapy treatment, comprising the steps of:

measuring X-ray data, including tissue peak dose ratios, scatter factors and tissue air dose ratios, concerning said X-ray from said X-ray source in advance by a detector;

storing said X-ray data in an X-ray data section of a computer;

calculating, on the basis of said X-ray data stored in said X-ray data section by a contribution distribution calculating section of said computer, contribution factors indicating a degree to which respective neighboring points in the body of the patient contribute to the dose at the point of concern;

taking a computed tomography image of the body of the patient on whom the radiation therapy treatment is planned;

calculating first electron density data at the respective neighboring points in the body of the patient in advance on the basis of a darkness in the computed tomography image of the body of the patient;

storing a density distribution data section of said computer with said first electron density data;

entering second electron density data of a plurality of typical patient models in a region classification section of said computer;

calculating, on the basis of said second electron density data of a plurality of typical patient models in advance by said region classification section, classification data of respective neighboring points in each of the typical patient models depending on the class of the X-ray causing emission of electron beam which gives energy to the point of concern, and storing said region classification section with said classification data;

selecting said classification data in connection with one of the typical patient models on the basis of the similarity with said first electron density stored in said density distribution data section by said region classification section; and calculating the dose at the point of concern on the basis of said contribution factors calculated by said contribution distribution calculating section, said first electron density data stored in said density distribution data section, and said classification data of the typical patient model selected in said region classification section by a dose calculating section of said computer.

20. A radiation therapy treatment planning method for calculating dose at a point of concern in a body of a patient irradiated with X-ray from an X-ray source, in a radiation therapy treatment, comprising the steps of:

measuring X-ray data, including tissue peak dose ratios and percentage depth doses, concerning said X-ray from said X-ray source in advance by a detector;

storing said X-ray data in an X-ray data section of a computer;

calculating, on the basis of said X-ray data stored in said X-ray data section by a contribution distribution calculating section of said computer, contribution factors indicating a degree to which respective neighboring points in the body of the patient contribute to the dose at the point of concern;

taking a computed tomography image of the body of the patient on whom the radiation therapy treatment is planned;

calculating first electron density data at the respective neighboring points in the body of the patient in advance on the basis of a darkness in the computed tomography image of the body of the patient;

storing a density distribution data section of said computer with said first electron density data;

entering second electron density data of a plurality of typical patient models in a region classification section of said computer;

calculating, on the basis of said second electron density data of a plurality of typical patient models in advance by said region classification section, classification data of respective neighboring points in each of the typical patient models depending on the class of the X-ray causing emission of electron beam which gives energy to the point of concern, and storing said region classification section with said classification data;

selecting said classification data in connection with one of the typical patient models on the basis of the similarity with said first electron density stored in said density distribution data section by said region classification section; and calculating the dose at the point of concern on the basis of said contribution factors calculated by said contribution distribution calculating section, said first electron density data stored in said density distribution data section, and said classification data of the typical patient model selected in said region classification section by a dose calculating section of said computer.

21. The method of claim 19, wherein said region classification section classifies the region in accordance with whether the principal X-ray causing emission of electron beam giving energy to the point of concern is the irradiated X-ray from said X-ray source, the first scattered X-ray due to Compton scattering caused by the irradiated X-ray from said X-ray source, or the multiple scattered X-ray having experienced more than one Compton scattering caused by the irradiated X-ray from said X-ray source.

22. The method of claim 19, wherein said region classification section selects one of the typical patient models which is most similar to the body of the patient on whom the radiation therapy treatment is planned, and outputs said classification data of the selected patient model to said dose calculation section.

23. The method of claim 20, wherein said region classification section classifies the region in accordance with whether the principal X-ray causing emission of electron beam giving energy to the point of concern is the irradiated X-ray from said X-ray source, the first scattered X-ray due to Compton scattering caused by the irradiated X-ray from said X-ray source, or the multiple scattered X-ray having experienced more than one Compton scattering caused by the irradiated X-ray from said X-ray source.

24. The method of claim 20, wherein said region classification section selects one of the typical patient models which is most similar to the body of the patient on whom the radiation therapy treatment is planned, and outputs said classification data of the selected patient model to said dose calculation section.

* * * * *